(12) United States Patent
Couvillon, Jr.

(10) Patent No.: US 7,077,808 B2
(45) Date of Patent: Jul. 18, 2006

(54) ULTRASONIC IMAGING CATHETER

(75) Inventor: Lucien Alfred Couvillon, Jr., Concord, MA (US)

(73) Assignee: Boston Scientific Scimed. Inc., Maple Grove, MN (US)

( * ) Notice: Subject to any disclaimer, the term of this patent is extended or adjusted under 35 U.S.C. 154(b) by 232 days.

(21) Appl. No.: 10/631,872

(22) Filed: Jul. 31, 2003

(65) Prior Publication Data

US 2005/0027198 A1    Feb. 3, 2005

(51) Int. Cl.
     *A61B 8/12*      (2006.01)

(52) U.S. Cl. ..................................... 600/466

(58) Field of Classification Search ........ 600/459–471, 600/101, 103
See application file for complete search history.

(56) References Cited

U.S. PATENT DOCUMENTS

| | | | |
|---|---|---|---|
| 4,546,771 A * | 10/1985 | Eggleton et al. | 600/437 |
| 5,000,185 A | 3/1991 | Yock | 128/662.03 |
| 5,250,167 A | 10/1993 | Adolf et al. | 204/299 |
| 5,268,082 A | 12/1993 | Oguro et al. | 204/282 |
| 5,372,138 A | 12/1994 | Crowley et al. | 128/662.06 |
| 5,377,685 A | 1/1995 | Kazi et al. | 128/662.06 |
| 5,389,222 A | 2/1995 | Shahinpoor | 204/299.2 |
| 5,556,700 A | 9/1996 | Kaneto et al. | 428/332 |
| 5,631,040 A | 5/1997 | Takuchi et al. | 427/100 |
| 5,651,366 A | 7/1997 | Liang et al. | 128/662.06 |
| 5,682,897 A | 11/1997 | Pomeranz | 128/662.06 |
| 5,771,902 A | 6/1998 | Lee et al. | 128/897 |
| 5,855,565 A | 1/1999 | Bar-Cohen et al. | 604/104 |
| 5,865,178 A | 2/1999 | Yock | 128/660.03 |
| 5,897,522 A | 4/1999 | Nitzan | 604/20 |
| 5,938,609 A | 8/1999 | Pomeranz | 600/439 |
| 6,060,811 A | 5/2000 | Fox et al. | 310/311 |
| 6,074,349 A | 6/2000 | Crowley | 600/463 |
| 6,109,852 A | 8/2000 | Shahinpoor et al. | 414/1 |
| 6,200,269 B1 | 3/2001 | Lin et al. | 600/466 |
| 6,248,074 B1 | 6/2001 | Ohno et al. | 600/463 |
| 6,249,076 B1 | 6/2001 | Madden et al. | 310/363 |

(Continued)

FOREIGN PATENT DOCUMENTS

EP      0 139 574      5/1985

(Continued)

OTHER PUBLICATIONS

Jose-Maria Sansinena et al., *Electroactive Polymer (EAP) Actuators as Artificial Muscles*, chap. 7, Conductive Polymers (SPIE Press, 2001), pp. 193-221.

(Continued)

*Primary Examiner*—Francis J. Jaworski
(74) *Attorney, Agent, or Firm*—Mayer & Williams PC; David B. Bonham, Esq.

(57) ABSTRACT

An ultrasonic imaging catheter apparatus and a method of using the same to scan the inner wall of a body lumen. The ultrasonic imaging catheter apparatus comprises: (a) a flexible elongate element adapted for insertion into a body lumen, the elongate element having distal and proximal ends; (b) an ultrasonic transducer generating and detecting ultrasonic energy disposed proximate the distal end of the elongate element; (c) a reflective member disposed proximate the ultrasonic transducer and optionally rotatable with respect to an axis of the body lumen, wherein the reflective member is adapted to reflect (i) ultrasonic energy generated by the ultrasonic transducer to a wall of the body lumen and (ii) ultrasonic energy reflected by the wall back to the transducer; and (d) an actuator, for example, an electroactive polymer actuator, adapted to change the angle of incidence of the ultrasonic energy relative to the reflective member.

17 Claims, 4 Drawing Sheets

U.S. PATENT DOCUMENTS

| | | | |
|---|---|---|---|
| 6,376,971 B1 | 4/2002 | Pelrine et al. | 310/363 |
| 6,457,365 B1 | 10/2002 | Stephens et al. | 73/626 |
| 6,514,237 B1 | 2/2003 | Maseda | 604/533 |
| 6,540,677 B1 | 4/2003 | Angelsen et al. | 600/437 |
| 6,543,110 B1 | 4/2003 | Pelrine et al. | 29/25.35 |
| 6,545,384 B1 | 4/2003 | Pelrine et al. | 310/309 |
| 6,583,533 B1 | 6/2003 | Pelrine et al. | 310/309 |
| 6,586,859 B1 | 7/2003 | Kornbluh et al. | 310/309 |
| 2002/0120297 A1 | 8/2002 | Shadduck | 607/2 |

FOREIGN PATENT DOCUMENTS

WO     WO 01/58973 A2     8/2001

OTHER PUBLICATIONS

David L. Brock, "Review of Artificial Muscle based on Contractile Polymers." www.ai.mit.edu/projects/muscle/papers/memo1330/memo1330html.

Edwin H. Jager et al., "Microfabricating Conjugated Polymer Actuators," *Science*, vol. 290, Nov. 24, 2000, pp. 1540-1545.

Yoseph Bar-Cohen, "Transition of EAP material from novelty to practical applications —are we there yet?" *Smart Structures and Materials 2001: Electroactive Polymer Actuators and Devices*, Yoseph Bar-Cohen, ed., Proceedings of SPIE, vol. 4329, 1-6.

American Medical Systems. Important for Paients Considering an Acticon Neosphincter. www.fda.gov/ohrms/dockets/ac/01/briefing/377b1_02_patient%20info.

Yoseph Bar-Cohen, Chap. 1, EAP History, Current Status, and Infrastructure, *EAP Actuators as Artificial Muscles* (SPIE Press, 2001), pp. 3-44.

Yoseph Bar-Cohen, ed., *Electroactive Polymer (EAP) Actuators as Artificial Muscles: Reality, Potential, and Challenges*, chap. 16: Application of Dielectric Elastomer EAP Actuators, SPIE Press (2001), pp. 457-495.

Yoseph Bar-Cohen, ed., *Electroactive Polymer (EAP) Actuators as Artificial Muscles: Reality, Potential, and Challenges*, Chap. 21 EAP Applications, Potential, and Challenges. SPIE Press (2001), pp. 615-659.

WorldWide ElectroActive Polymers (Artificial Muscles) Newsletter, vol. 3, No. 1 (Jun. 2001), pp. 1-14.

John D.W. Madden et al., "Polyprrole Actuators: Modeling and Performance," *Smart Structures and Materials 2001: Electroactive Polymer Actuators and Devices*, Yoseph Bar-Cohen, ed., SPIE Proceedings, vol. 4329 (Mar. 5-8, 2001), pp. 72-83.

Ron Pelrine, "Applications of Dielectric Elastomer Actuators," *Smart Structures and Materials 2001: Electroactive Polymer Actuators and Devices*, Yoseph Bar-Cohen, ed., SPIE Proceedings vol. 4329 (Mar. 5-8, 2001), pp. 335-349.

John D.W. Madden et al., "Conducting Polymer Actuators as Engineer Materials," *Smart Structures and Materials 2002: Electroactive Polymer Actuators and Devices*, Yoseph Bar-Cohen, ed, SPIE Proceedings, vol. 4695 (2002), pp. 176-190.

Eniko T. Enikov et al., "Electrotransport and Deformation Model of Ion Exchange Membrane based Actuators," *Smart Structures and Materials 2000: Electroactive Polymer Actuators and Devices*, Yoseph Bar-Cohen, ed, SPIE Proceedings, vol. 3987 (2000), pp. 129-139.

Rainer W. Gulch et al., "Electrochemical Stimulation and Control of Electroactive Polymer Gels," *Smart Structures and Materials 2001: Electroactive Polymer Actuators and Devices*, Yoseph Bar-Cohen, ed, SPIE Proceedings, vol. 4329 (2001), pp. 328-334.

T. Hagiwara et al., "Enhancement of the Electrical Conductivity of Polypyrrole Film by Stretching: Influence of the Polymerization Conditions," *Synthetic Metals*, vol. 36 (1990) pp. 241-252.

Yamaura, M., et al., "Enhancement of Electrical Conductivity of Polypyrrole Film By Stretching: Counter Ion Effect," *Synthetic Metals*, vol. 26 (1988) pp. 209-224.

\* cited by examiner

ULTRASONIC IMAGING CATHETER

FIELD OF THE INVENITON

This invention relates to catheters appropriate for imaging, and more particularly to catheters appropriate for intravascular ultrasonographic imaging applications.

BACKGROUND OF THE INVENTION

Intravascular ultrasound (IVUS) catheters and methods for imaging are known. For example, U.S. Pat. No. 5,000,185 to Yock, the entire disclosure of which is incorporated by reference, discloses devices and methods for high-resolution intravascular ultrasound imaging to assist with the administration of vascular interventional therapy and to monitor the results of such therapy. In Yock, an ultrasonic transducer is carried by the distal end of a catheter adapted for insertion into a blood vessel, whereupon either the transducer or another element, such as an ultrasound mirror, is rotated and/or translated relative to the catheter to image different portions of the vessel.

In spite of advances in the art, however, there continues to be a need for a catheter apparatus that can provide longitudinal scans of a vessel surface along the axis of the vessel, and oblique scans which examine vessel regions distal of the catheter tip, without the need for an accompanying longitudinal movement of the transducer or other catheter element along vessel axis.

SUMMARY OF THE INVENTION

The above and other needs of the prior art are addressed by the present invention. According to an embodiment of the present invention, an ultrasonic imaging catheter apparatus is provided, which comprises the following: (a) a flexible elongate body adapted for insertion into a body lumen, the elongate body having distal and proximal ends; (b) an ultrasonic transducer generating and detecting ultrasonic energy disposed proximate the distal end of the elongate body; (c) a reflective member disposed proximate the ultrasonic transducer and which is optionally rotatable with respect to an axis of the body lumen, wherein the reflective member is adapted to reflect (i) ultrasonic energy generated by the ultrasonic transducer to a wall of the body lumen and (ii) ultrasonic energy reflected by the wall back to the transducer; and (d) an actuator, such as an electroactive polymer actuator, the electroactive polymer actuator being adapted to electronically control the tilt of the reflector and thus the angle of incidence of the ultrasonic energy upon the reflective member.

Where used in connection with the present invention, the electroactive polymer actuators typically comprise an electroactive polymer region, a counter-electrode region, and an electrolyte-containing region disposed between the electroactive polymer region and the counter-electrode region. Beneficial electroactive polymers for these embodiments include polyaniline, polysulfone, polyacetylene and polypyrrole.

In some embodiments, the control signals for the ultrasonic transducer and for the electroactive polymer actuator are transmitted via a shared single electrical conduction path, for example a coaxial cable. In such embodiments, it is beneficial to provide the ultrasonic transducer with a high pass filter to block passage of low-frequency/dc electroactive polymer actuator control signals, and to provide the electroactive polymer actuator with a low pass filter to block passage of high-frequency ultrasonic transducer control signals.

The entire catheter assembly, including the reflective member, transducer and electroactive polymer, are rotated in some embodiments. In these and other embodiments, the catheter apparatus can further comprise a motor and a drive shaft for translating torque from the motor, for example, through a suitable connector or rotary joint, thereby rotating the reflective member, among other elements.

Other aspects of the present invention are directed to methods of scanning the inner wall of a body lumen. These methods comprise: (a) providing a catheter apparatus like that above; (b) sweeping the ultrasonic energy from the transducer in a pattern over the interior wall of the body lumen by operating the electroactive polymer actuator to change the angle of incidence of the ultrasonic energy upon the reflective member, and by optionally rotating the reflective member; (c) receiving ultrasonic energy reflected from the interior wall of the body lumen; and (d) producing an image from the reflected ultrasonic energy. For example, the ultrasonic energy can be directed at a forward angle between about 10° to about 85° relative to the axis of the body lumen, such that a conical forward sweep is performed.

One advantage of the present invention is that catheters, systems and methods are provided for intravascular ultrasonography.

Another advantage of the present invention is that catheters for intravascular ultrasonography are provided, in which the wall of an adjacent body lumen can be axially (longitudinally) scanned, without the need for axial movement of the transducer or other element relative to the body lumen.

Another advantage of the invention is that catheters for intravascular ultrasonography are provided, which can provide for forward, lateral and retrograde scanning, without the need for axial movement of the transducer or other element relative to the body lumen.

Additional embodiments and advantages of the invention will become readily apparent to those of ordinary skill in the art upon review of the following detailed description in which the preferred embodiments are set forth in detail.

DESCRIPTION OF THE SPECIFIC EMBODIMENTS

The present invention now will be described more fully hereinafter with reference to the accompanying drawings, in which preferred embodiments of the present invention are shown. This invention may, however, be embodied in different forms and should not be construed as limited to the embodiments set forth herein.

Figure 1A:
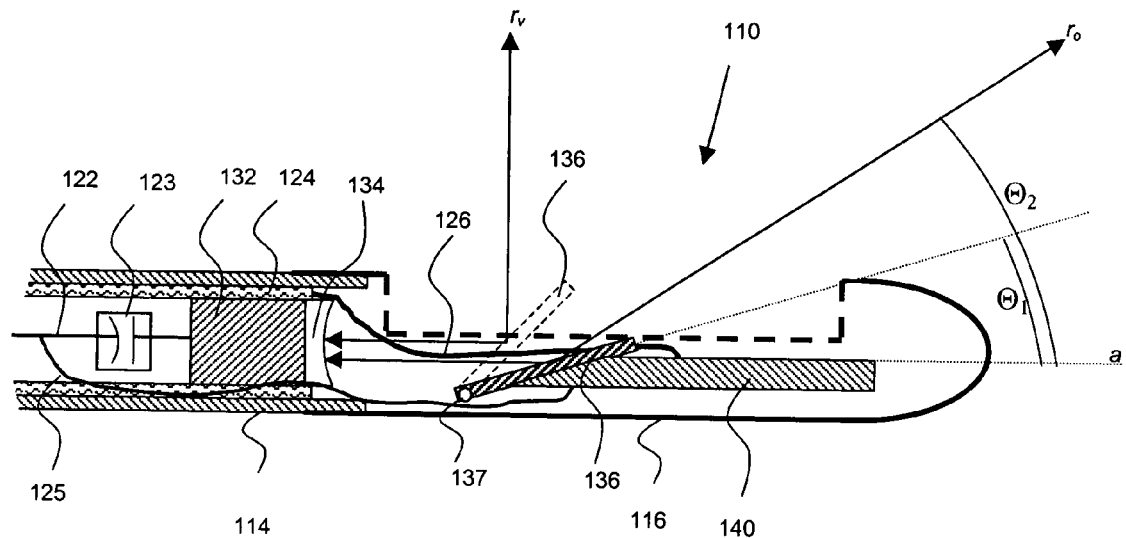
FIG. 1A is a schematic partial cross-sectional view of the distal end of a catheter apparatus, in accordance with an embodiment of the present invention.

Referring now to FIG. 1A, and in accordance with one aspect of the present invention, a distal portion of a catheter apparatus 110 is illustrated, which is adapted for insertion into a body lumen, for example, a blood vessel within the coronary vasculature.

In the embodiment shown, an ultrasonic transducer 132, an associated ultrasonic lens 134, and a reflective member 136 are carried at the distal end of a flexible shaft of catheter apparatus 110. An electrical system (described in more detail below) is connected to the ultrasonic transducer 132 for supplying signals to and receiving signals from the transducer 132 during operation. The electrical system also supplies signals to an actuator 140, which is used to change the angle at which ultrasonic waves are incident upon the reflective member 136 during operation. The various elements of the catheter apparatus 110 are typically rotated during operation by means of mechanical torque, which is transmitted along drive shaft 114.

The ultrasonic transducer 132 can be formed, for example, using any of a number of materials that are known in the art. For instance, single crystals, which are capable of operating at a frequency range of, for example, 5 to 50 megahertz, are known in the art. Typical materials for forming such crystals include barium titanate or cinnabar. Conductive electrodes, for example, films of gold or other conductive metals, may be provided on opposing surfaces of the crystal. If desired, oscillations from the backside of the crystal can be damped as is known in the art, for example, through the use of a suitable backing material. Of course, other materials are known besides piezoelectric crystal oscillators for the formation of ultrasonic transducers. For example, organic materials such as polyvinylidene difluoride (PVDF) and vinylidene fluoride-trifluoroethylene copolymers are known, which may also be used to form the ultrasonic transducer.

The ultrasonic transducer is also provided with an ultrasonic lens 134, as is known in the art. In the embodiment illustrated in FIG. 1A, the ultrasonic transducer 132 is mounted within the end of drive shaft 114, although many other placement locations are clearly possible. For example, the ultrasonic transducer 132 can be mounted to housing 116, if desired.

A reflective member 136 is also disposed in the catheter apparatus 110. The reflective member 136 can be, for example, an ultrasonographic mirror made, for example, from metal such as stainless steel or a hard polymer such as polycarbonate with high reflectivity at ultrasound frequencies, as is known in the art. Reflective member 136 is disposed within the catheter apparatus 110 such that the energy generated by the transducer 132 is reflected into the tissue of an adjacent body lumen (not shown). Some of this energy will rebound from the lumen tissue, to be again reflected by the reflective member 136 back to the transducer 132.

More particularly, in the configuration illustrated in FIG. 1A, a signal generated by the transducer 132 travels axially until is meets reflective member 136, at which point the signal is deflected at an angle $\theta_2$ from the device axis $\alpha$ (see oblique ray $r_o$). Note that, in this embodiment, the angle at which the signal is deflected relative to the device axis $\alpha$ is equal to 2 times the angle $\theta_1$ at which the reflective member 136 is tilted from the device axis $\alpha$. For example, by tilting the reflective member 45 degrees from the device axis $\alpha$ (i.e., $\theta_1=45°$, see position of reflective member 136 designated by dashed lines), the signal from the transducer 132 is deflected in a direction orthogonal to the device axis $\alpha$ (i.e., in a direction where $\theta_2=90°$; see vertical ray $r_v$). By tilting the reflective member to more than 45 degrees from the device axis $\alpha$ (i.e., $\theta_1>45°$, not illustrated) the signal from the transducer 132 will be deflected rearward of the point at which the ultrasound energy is incident upon the reflective member 136. The angle of inclination of the reflective member 136 can vary widely, typically ranging from 10° to 80°, more typically from 10° to 40° relative to the axis a, thereby providing a forward view.

In the embodiment illustrated in FIG. 1A, the reflective member 136 is mounted distal to the transducer 132. However, alternate embodiments are clearly possible, including those in which the reflective member 136 is provided at a position that is proximal to the ultrasonic transducer 132.

As illustrated in FIG. 1A, catheter apparatus 110 includes a housing 116 attached to the end of drive shaft 114. The drive shaft 114 in this embodiment is of a flexible construction, which allows the catheter apparatus 110 to be guided along tortuous paths, for example, blood vessels of the coronary, peripheral or cerebral vasculature. The drive shaft 114 is also engineered with sufficient strength to translate mechanical torque along its length and rotate the housing 116 at a desired rotational rate. An example of an appropriate drive shaft material for use in connection with the present invention is a counterwound multifilar structure with good torque fidelity, as disclosed in U.S. Pat. No. 5,372,138, to Crowley et al, the entire disclosure of which is incorporated by reference.

Figure 3:
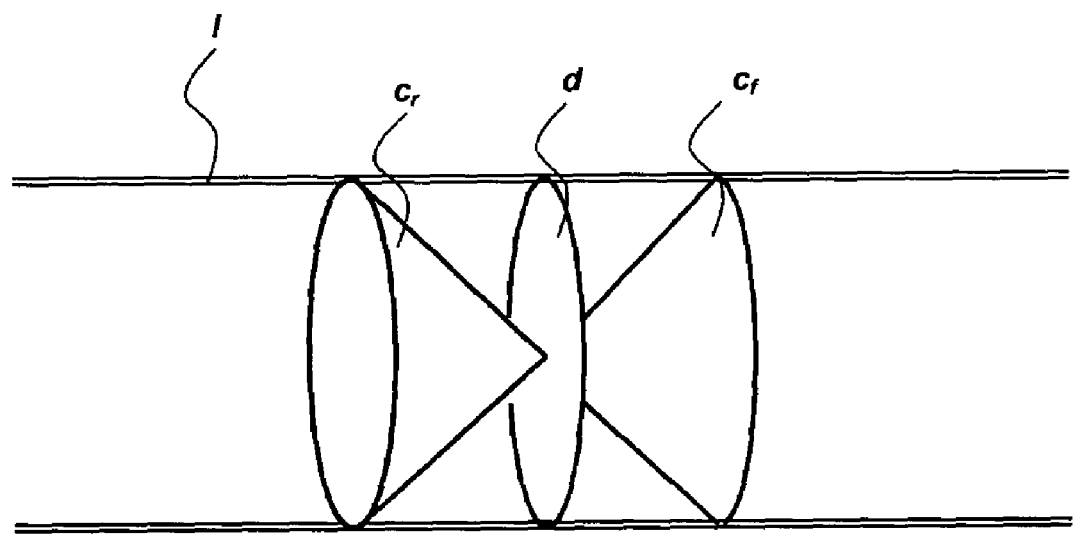
FIG. 3 is schematic diagram illustrating three scanning sections, which can be generated using a catheter apparatus in accordance with the present invention.

In this connection, a motor drive (not shown) is provided in this embodiment for rotating the drive shaft 114, although manual rotation may also be employed. By rotating the drive shaft, the transducer signal can be swept in a desired pattern, providing, for example, a 360° conical scan of the body lumen. As schematically illustrated in FIG. 3, by appropriately tilting the reflective member, the angle of the conical scan of a body lumen l can be swept, for example, between a forward conical scan $c_f$ to a lateral disc d to a rearward conical scan $c_r$.

Figure 2:
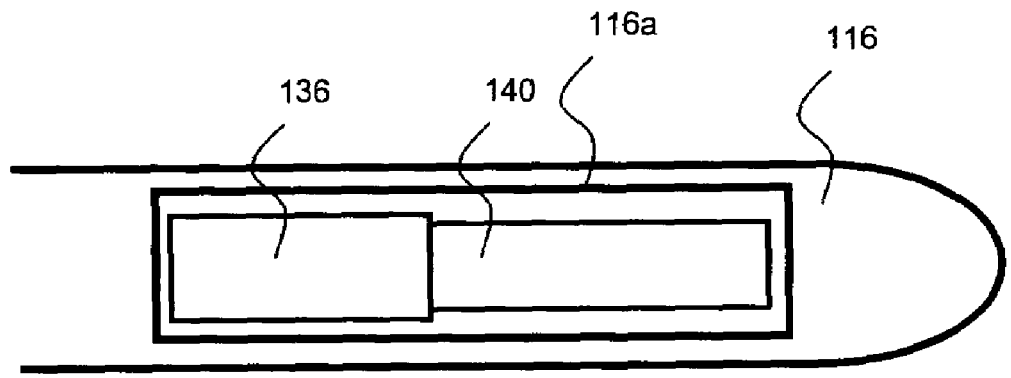
FIG. 2 is a schematic top view of the distal portion of FIG. 1A.

The housing 116 in the embodiment of FIG. 1A is provided with a cutout 116a (see FIG. 2), which provides an aperture through which ultrasonic energy can be directed without interference from reflective member 136 to a body lumen wall, and back. However, it is also possible to form the housing 116 of a material that causes minimal attenuation of the ultrasonic signal that is transmitted and received by transducer 132. Suitable low-attenuation materials include polyethylene, silicone rubber, polyvinyl chloride, polyurethanes, polyesters, natural rubbers, and the like.

It is frequently beneficial to provide the catheter apparatus 110 illustrated in FIG. 1A with within an outer protective sheath. The outer protective sheath can be formed from a variety of materials, for example, materials such as those listed in the prior paragraph. Although every element of the catheter assembly 110 illustrated in the embodiment of FIG. 1a is adapted to rotate en masse, it is desirable in many embodiments to provide the catheter assembly 110 within an outer protective sheath that does not rotate, as is known in the art.

A coaxial cable is provided within the drive shaft 114 in the embodiment of FIG. 1A. As is typical, the coaxial cable includes two conductors—a core conductor 122, commonly a wire such as a copper wire, and an outer annular shield or conductor 124, commonly a wire braid such as a copper wire braid. Coaxial cable is advantageous due to the low attenuation and good electromagnetic shielding associated with the same, particularly at higher frequencies. In the embodiment illustrated, a current path is established form the core conductor 122 to the actuator 140 via conductive line 125, while another current path is established between the annular conductor 124 and the actuator 140 via conductive line 126.

In accordance with the embodiment illustrated, the coaxial conductors 122, 124 carry at least two groups of signals. Members of the first group of signals are high frequency signals, which are transmitted to and from the ultrasonic transducer 132. Members of the second group of signals are low frequency or dc signals, which are transmitted to the actuator. In this embodiment, it is beneficial to provide a high pass filter, e.g., a simple capacitor blocking 123, to isolate the transducer 132 from the low frequency actuator signals. It may also be beneficial to utilize a low pass filter, e.g., a simple inductor (not shown), to isolate the actuator 140 from the high frequency transducer signals.

In FIG. 1A, the housing 116 is provided with an assembly comprising a reflective member 136 that is rotatable (i.e., tiltable) about an axis established by a mechanical pivot 137, which axis is orthogonal to the longitudinal axis a of the catheter assembly 110 in the embodiment illustrated. Although a pivot 137 is illustrated, numerous other configurations are possible, including simply mounting the reflective member 136 on a member that can be repeatedly flexed as required. The angle of tilt of the reflective member 136 is adjusted in the embodiment of FIG. 1A using a single actuator 140, although multiple actuators can obviously be employed, if desired.

The actuators used in connection with the endoscopes of the present invention are typically electrically controlled actuators (as used herein, "electrically controlled actuators" include those actuators that are activated by photons) such as piezoelectric activators, shape memory activators and/or electroactive polymer actuators, with actuators based on electroactive polymers being preferred.

Members of the family of plastics referred to as "conducting polymers," electroactive polymers are polymers characterized by their ability to change shape in response to electrical stimulation. They commonly feature a conjugated backbone and have the ability to increase electrical conductivity under oxidation or reduction.

Some common electroactive polymers are polyaniline, polysulfone, polypyrrole and polyacetylene. Polypyrrole is pictured below:

These materials are typically semi-conductors in their pure form. However, upon oxidation or reduction of the polymer, conductivity is increased. The oxidation or reduction leads to a charge imbalance that, in turn, results in a flow of ions into the material in order to balance charge. These ions, or dopants, enter the polymer from an ionically conductive electrolyte medium associated with the electroactive polymer or are redistributed within the polymer. The electrolyte may be, for example, in the form of a gel, a solid, or a liquid. If ions are already present in the polymer when it is oxidized or reduced, they may exit the polymer.

It is well known that dimensional changes may be effectuated in certain conducting polymers by the mass transfer of ions into or out of the polymer. For example, in some conducting polymers, expansion is due to ion insertion between chains, whereas in others inter-chain repulsion is the dominant effect. Regardless of the mechanism, the mass transfer of ions into and out of the material leads to an expansion or contraction of the polymer.

Currently, linear and volumetric dimensional changes on the order of 25% are possible. The stress arising from the dimensional change can be on the order of 3 MPa, far exceeding that exerted by smooth muscle cells, allowing substantial forces to be exerted by actuators having very small cross-sections. These characteristics are ideal for construction of the devices of the present invention.

Figure 5:
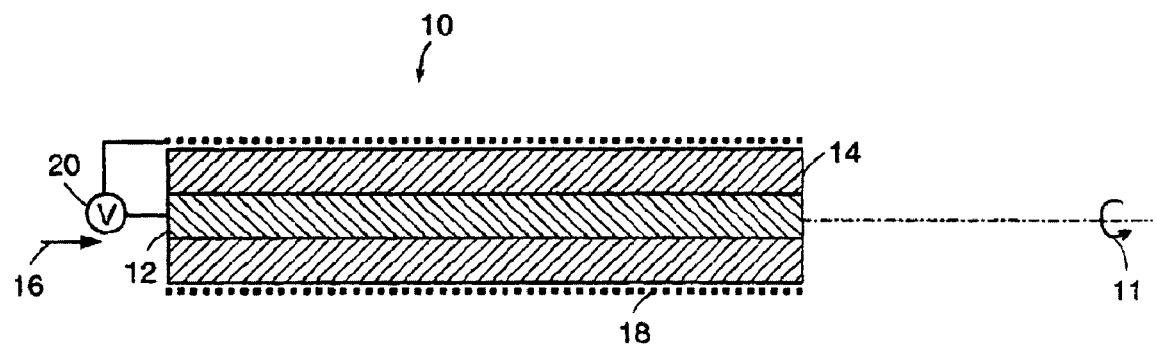
FIG. 5 is a schematic cross-sectional view of an electroactive polymer actuator useful in connection with the present invention.

Referring now to FIG. 5, an electroactive polymer actuator 10 is shown schematically in cross-section. Active member 12 of actuator 10 has a surface coupled with electrolyte 14 and has an axis 11. Active member 12 includes an electroactive polymer that contracts or expands in response to the flow of ions out of, or into, the active member 12. Ions are provided by electrolyte 14, which adjoins member 12 over at least a portion, and up to the entirety, of the surface of active member 12 in order to allow for the flow of ions between the two media.

Many geometries are available for the relative disposition of member 12 and electrolyte 14. In accordance with some embodiments of the invention, member 12 may be a film, a group of films, a fiber, a group of fibers, or a combination of the same disposed so as to act collectively to apply a force in a longitudinal direction substantially along axis 11 in this instance.

Active member 12 includes an electroactive polymer. Many electroactive polymers having desirable properties are known to persons of ordinary skill in the art. In accordance with some embodiments of the invention, active member 12 can be a polypyrrole film. Such a polypyrrole film may be synthesized, for example, by electrodeposition according to the method described by M. Yamaura et al., "Enhancement of Electrical Conductivity of Polypyrrole Film by Stretching: Counter-ion Effect," Synthetic Metals, vol. 36, pp. 209–224 (1988), which is incorporated herein by reference. In addition to polypyrrole, any conducting polymer that exhibits contractile or expansile properties may be used within the scope of the invention. Polyaniline, polysulfone, polyacetylene are examples.

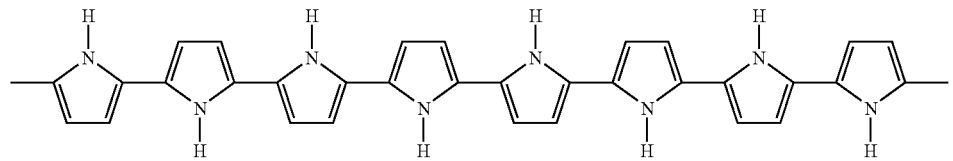

Electrolyte 14 may be, for example, a liquid, a gel, or a solid, so long as ion movement is allowed. Moreover, where the electrolyte 14 is a solid, it will typically move with the active member 12 and will typically not be subject to delamination. Where the electrolyte 14 is a gel, it may be, for example, an agar or polymethylmethacrylate (PMMA) gel containing a salt dopant. Where the electrolyte is a liquid, it may be, for example, a phosphate buffer solution, KCl, NaCl and so forth. The electrolyte may be non-toxic in the event that a leak inadvertently occurs in vivo.

Counter electrode 18 is in electrical contact with electrolyte 14 in order to provide a return path for charge to a source 20 of potential difference between member 12 and electrolyte 14. Counter electrode 18 may be any suitable electrical conductor, for example, another conducting polymer, a conducting polymer gel, or a metal such as gold or platinum, which can be, for example, in wire or film form and can be applied, for example, by electroplating, chemical deposition, or printing. In order to activate actuator 10, a current is passed between active member 12 and counter electrode 18, inducing contraction or expansion of member 12. Additionally, the actuator may have a flexible skin for separating the electrolyte from an ambient environment.

The actuator can be provided in an essentially infinite array of configurations as desired, including planar actuator configurations (e.g., with planar active members and counter-electrodes), cylindrical actuator configurations (e.g., see the actuator illustrated in FIG. 5, which is illustrated as having a cylindrical active member and wire coil counter electrode), and so forth.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72–83), both of which are hereby incorporated by reference in their entirety.

One or more actuators 140 can be used to change the deflection angle associated with the reflective member 136. Moreover, these actuators 140 can be associated with the reflective member 136 in a wide range of configurations. For example, in the embodiment illustrated in FIG. 1A, the angle of inflection of the reflective member 136 increases upon lengthwise expansion of the actuator 140, and decreases upon lengthwise contraction of the actuator 140. For this purpose, an elongated column of electroactive polymer material can be used in connection with an actuator design like that of FIG. 5.

However, myriad other designs are also possible. For example, an actuator having substantial tensile strength, but negligible column strength, can be placed in tension with a reflective member that is in mechanical communication with a spring element. For example, referring again to the catheter apparatus of FIG. 1A, the hinge 137 can be provided with a spring element which urges the mirror in a counterclockwise direction. In such an embodiment, as above, the angle of incidence is controlled based on the degree of contraction or expansion of the actuator 140, with expansion of the actuator 140 leading to a greater angle of incidence, and contraction leading to a lesser angle of incidence.

Figure 6:
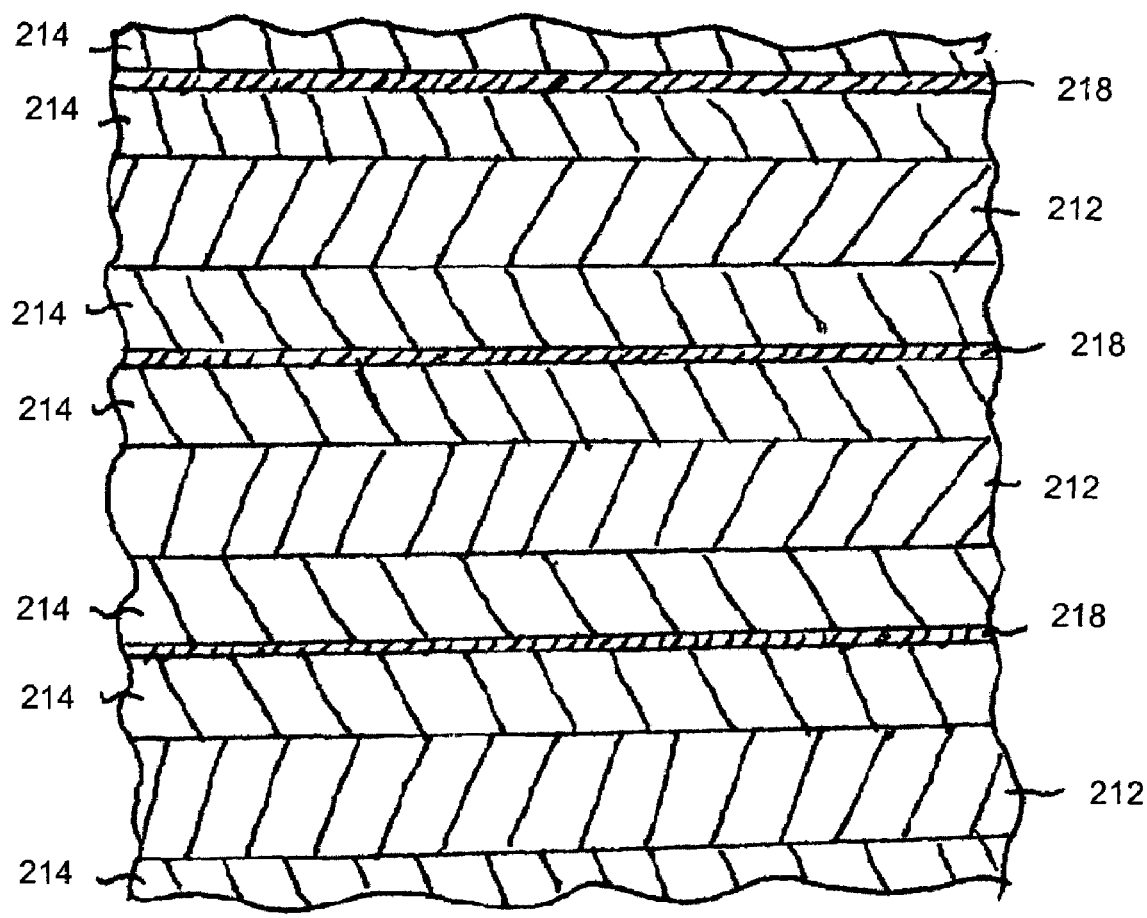
FIG. 6 is a schematic cross-sectional view of another electroactive polymer actuator configuration useful in connection with the present invention.

As another example, FIG. 6 provides a schematic cross-sectional view of an electroactive polymer layer stack, which can be used in the formation of an expandable actuator 140. Referring now to FIG. 6, a stack of counter-electrode layers 218, active layers 212 and electrolyte-containing layers 214 are shown. As above, the counter-electrode layers 218 may be formed from a suitable electrical conductor, for example, a metal such as gold or platinum. The electrolyte within the electrolyte-containing layers 214 can be, for example, a liquid, a gel, or a solid, with appropriate measures being taken, where needed, to prevent short-circuiting between the counter-electrodes 218 and the active layers 212. The active layer 212 comprises an electroactive polymer, for example, polypyrrole, polysulfone, polyacetylene or polyaniline. The actively layers 212 can also optionally be provided with conductive electrical contacts (not shown), if desired, to enhance electrical contact with the control system. During operation, an appropriate potential difference is applied across the active layers 212 and the counter-electrode layers 218. Typically, all of the active layers 212 are shorted to one another, as are all of the counter-electrode layers 218, allowing the active layers 212 to expand and contract simultaneously. As above, the electroactive polymer active layers 212 expand and contract upon establishing an appropriate potential difference between the active layers 212 and the counter-electrode layers 218. This, in turn, expands or contracts the actuator stack.

Figure 1B:
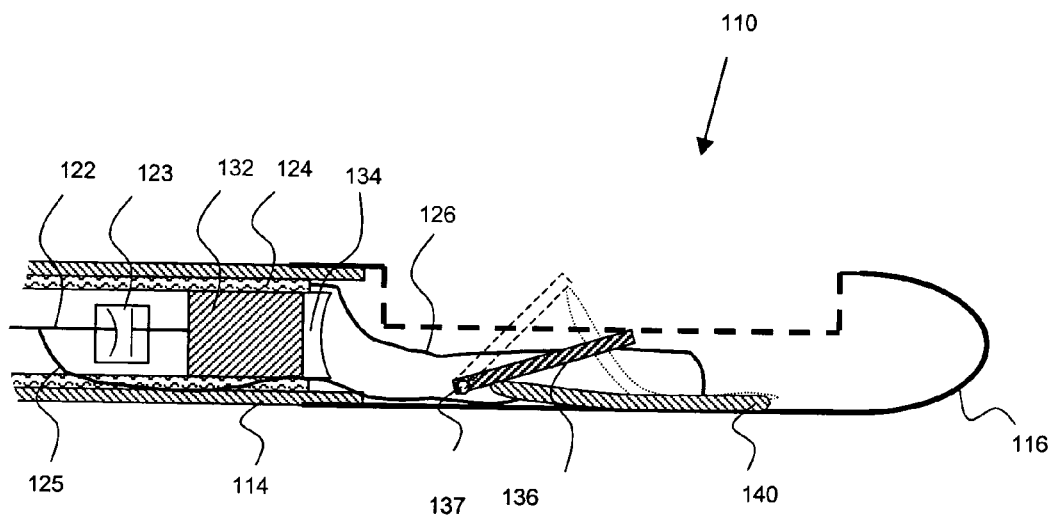
FIG. 1B is a schematic partial cross-sectional view of the distal end of a catheter apparatus, in accordance with another embodiment of the present invention.

As another example, electroactive polymer actuators are known in which an electroactive polymer is laminated between conductive layers to produce a bending-type actuation, with the degree of bending being dependent upon on the applied voltage. Such an actuator 140 is illustrated in FIG. 1B, wherein the angle at which the reflective member 136 is tilted increases with increasing bend of the actuator 140. For more information concerning such actuators, see, e.g., Pelrine et al., Smart Structures and Materials 2001: Electroactive Polymer Actuators and Devices, Yoseph Bar-Cohen, Ed., Proceedings of SPIE Vol. 4329 (5–8 Mar. 20001), pp. 335–349, which is hereby incorporated by reference. This reference also describes numerous other known electroactive polymer configurations, including extender, bowtie, diaphragm, spider, tube, and roll configurations, which can be used to change the deflection angle of a reflective member 136.

In many embodiments, the inclination angle of the reflective member is inferred, for example, from the intrinsic position-dependent electrical properties of the electroactive polymer actuator. However, one or more strain gauges may also be employed to provide electronic feedback regarding the inclination angle of the reflective member. This electronic feedback will also provide a number of additional advantages, including greater stability, error correction, and immunity from drift. Strain gauges suitable for use in the present invention include (a) feedback electroactive polymer elements whose impedance or resistance varies as a function of the amount of strain in the device, (b) linear displacement transducers (e.g., an iron slug slidably positioned in the core of a coil) and (c) conventional strain gauges in which the resistance of the device varies as a function of the amount of strain in the device, thus allowing the amount of strain to be readily quantified and monitored. Such strain gauges are commercially available from a number of different sources, including National Instruments Co., Austin, Tex., and include piezoresistive strain gauges (for which resistance varies nonlinearly with strain) and bonded metallic strain gauges (for which resistance typically varies linearly with strain).

Timing and control circuitry is also typically provided in connection with the above described catheter apparatus to control, for example, the operation of the ultrasonic transducer, the actuator, and the motor drive. A display is also typically provided, which is operated under the control of the timing and control circuitry for displaying image information.

Figure 4:
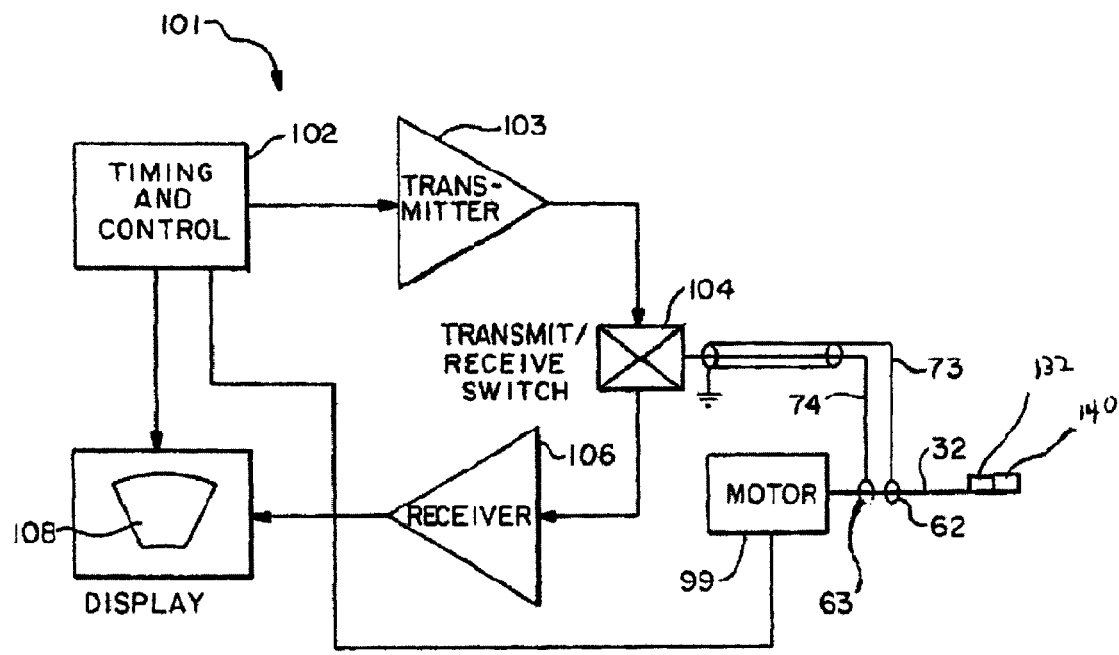
FIG. 4 is a schematic block diagram of the electrical components utilized in a catheter system, in accordance with an embodiment of the present invention.

In this connection, a schematic block diagram is presented in FIG. 4, which illustrates the electrical components utilized in a catheter system, in accordance with one embodiment of the present invention. As previously noted, the entire catheter apparatus, including the transducer 132, actuator 140, and the coaxial cable 32, rotates as a single unit in the embodiment described above. Electrical connection can nonetheless be established between these components and a non-rotating electrical system using methods known in the art. For example, electrical connections can be made as described in U.S. Pat. No. 5,000,185 by using a pair of spaced-apart rotating slip rings 62, 63, which are formed of a conducting material, and which are placed in electrical connection with the conductive members of the coaxial cable 32. A pair of spring-urged contacts, for example, conductive brushes, can be adapted to slidably engage the slip rings, which contacts are connected to conductors 73 and 74. Alternatively, a rotary transformer familiar in the art (not shown) may provide coupling with no moving parts.

Motor 99 is driven by and is under the control of electronic circuitry forming a part of electrical system 101. Such a system 101 includes a timing and control block 102, which supplies pulses to a transmitter 103. The output of the transmitter 103 is supplied through a transmit/receive switch 104 which supplies the signals through the conductors 73 and 74, through the slip rings 62 and 63, through the inner and outer conductors of the coaxial cable 32, and to the ultrasonic transducer 132 and the actuator 140 as described above. System 101 is capable of supplying high frequency energy to the ultrasonic transducer 132 and low frequency/dc energy to the actuator 140 via the transmitter 103, while at the same time driving the drive shaft 114 using motor 99, which is also under the control of the timing and control block 102. The motor 99 can be, for example, an open loop stepping motor or a closed drop servo-controlled motor that can be driven by the timing and control block 102.

As an alternative to the use of an external motor 99, it is also possible to construct catheters in accordance with the present invention, in which motor(s) are provided within the distal end of the catheter, allowing the reflective member to be rotated, for example. Also, as indicated above, the catheter can be manually rotated.

Voltage pulses for excitation of the transducer 132 commonly range, for example, from 10 to 50 volts. The transducer 132 produces ultrasonic waves which emanate therefrom, reflecting from the surface of the reflective member and into the surrounding tissue as described above. Portions of the ultrasonic sonic energy waves rebounding from the tissue are also reflected from the reflective member and back to the transducer 132, whereupon the transducer acts as a receiver, picking up ultrasonic waves and converting them into electrical signals which are supplied by the coaxial cable 32, to the slip rings 62 and 63, through the conductors 73 and 74, and through the transmit/receive switch 104 to a receiver 106. These signals are amplified and supplied to a display unit, which includes a display monitor 108 under the control of the timing and control block 102 to supply an image on the display 108.

Operation and use of the catheter apparatus and system is briefly described as follows. The catheter apparatus of the present invention is introduced into a body lumen of a patient, for example, into the femoral artery. In some embodiments, the catheter apparatus can be advanced over a guidewire as is known in the art. The progress of the catheter into the patient can be observed, for example, under x-ray fluoroscopy. The vessel wall itself can be viewed by suitable operation of system 101. This can be accomplished, for example, by operating the timing control block 102 to cause operation of the motor 99 which in turn causes rotation of the drive shaft. As a result, the transducer 132 and reflective member are allowed to scan the interior of the vessel in which the catheter is disposed, typically at a rotation rate which achieves a "real-time" scan, for example, 30 frames per second (i.e., 1800 frames, or rotations, per minute). Suitable rotation rates are thus typically in the range of 5 to 60 revolutions per second, i.e., 300 to 3600 rpm. An image of what is being scanned will appear on the screen 108 of the display device. Alternatively, the drive shaft may be manually rotated (or aimed without rotation) to provide a desired image. Generally, however, motorized rotation will provide a higher definition image. As in prior art systems, distinct cross-sectional images are successively produced as the catheter apparatus is advanced incrementally, allowing the operator to determine the length and topography of the region. In the present invention, however, a portion of the vessel length can also be longitudinally scanned by operating the actuator 140 to tilt the reflective member. As noted above, depending upon the angle of the reflective member, the scan can constitute a forward scan, a lateral scan, a rearward scan, or a combination of all three.

In addition to imaging capability, the catheters of the present invention may further include interventional capability, for example, for recanalization of occluded regions within the imaged blood vessel, as is known in the art. By recanalization is meant both the opening of total occlusions as well as the broadening of the vessel lumen in partial occlusions. Catheters combining ultrasonic imaging capability with atherectomy devices for severing of the stenotic material are described in detail in U.S. Pat. No. 5,000,185. Of course, the catheters of the present invention are not limited to use in atherectomy and can be used to perform a wide variety of other interventional techniques that are performed with vascular catheters. Suitable interventional techniques include balloon angioplasty, cutting balloons, laser ablation angioplasty, balloon embolectomy, aspiration embolectomy, heat probe ablation, abrasion, drilling, therapeutic ultrasound, and the like. Also, the catheters may be adapted for introducing clot-dissolving drugs, such as tissue plasminogen activator, streptokinase, or urokinase, in order to reduce the stenosis, as well as anti-restenosis drug which inhibit restenosis, such as paclitaxel.

Although various embodiments are specifically illustrated and described herein, it will be appreciated that modifications and variations of the present invention are covered by the above teachings and are within the purview of the appended claims without departing from the spirit and intended scope of the invention.

The invention claimed is:
1. An ultrasonic imaging catheter apparatus comprising:
a flexible elongate body adapted for insertion into a body lumen, the elongate body having distal and proximal ends;
an ultrasonic transducer disposed proximate said distal end of said elongate body, said ultrasonic transducer generating and detecting ultrasonic energy;
a reflective member proximate said ultrasonic transducer, said reflective member being adapted to reflect (a) ultrasonic energy generated by said ultrasonic trans- ducer to a wall of said body lumen and (b) ultrasonic energy reflected by said wall back to said transducer; and an actuator in mechanical communication with said reflective member, said actuator being adapted to change the angle of incidence of said ultrasonic energy relative to said reflective member, wherein control signals for said ultrasonic transducer and for said actuator are transmitted via a common electrical conductor.

2. The ultrasonic imaging catheter apparatus of claim 1, wherein said ultrasonic transducer is provided with a high pass filter to block said actuator control signals.

3. The ultrasonic imaging catheter apparatus of claim 2, wherein the high pass filter comprises a capacitor.

4. The ultrasonic imaging catheter apparatus of claim 1, wherein said actuator is provided with a low pass filter to block said ultrasonic transducer control signals.

5. The ultrasonic imaging catheter apparatus of claim 4, wherein the low pass filter comprises an inductor.

6. The ultrasonic imaging catheter apparatus of claim 1, wherein said common electrical conductor is a coaxial cable.

7. An ultrasonic imaging catheter apparatus comprising:
a flexible elongate body adapted for insertion into a body lumen, the elongate body having distal and proximal ends;
an ultrasonic transducer disposed proximate said distal end of said elongate body, said ultrasonic transducer generating and detecting ultrasonic energy;
a reflective member proximate said ultrasonic transducer, said reflective member being adapted to reflect (a) ultrasonic energy generated by said ultrasonic transducer to a wall of said body lumen and (b) ultrasonic energy reflected by said wall back to said transducer; and
an actuator in mechanical communication with said reflective member, said actuator being adapted to change the angle of incidence of said ultrasonic energy relative to said reflective member,
wherein said actuator is an electroactive polymer actuator.

8. The ultrasonic imaging catheter apparatus of claim 7, wherein said reflective member is rotatable with respect to an axis of said body lumen.

9. The ultrasonic imaging catheter apparatus of claim 8, wherein said ultrasonic transducer is rotatable with respect to said axis of said body lumen.

10. The ultrasonic imaging catheter apparatus of claim 8, further comprising a rotatable housing, wherein said reflective member and said electroactive polymer actuator are mounted within said housing.

11. The ultrasonic imaging catheter apparatus of claim 10, wherein the housing comprises a material that is substantially transparent to said ultrasonic energy.

12. The ultrasonic imaging catheter apparatus of claim 10, wherein said reflective member is provided with a mechanical hinge, wherein said mechanical hinge is secured to said housing, and wherein said electroactive polymer actuator is disposed between said housing and said reflective member.

13. The ultrasonic imaging catheter apparatus of claim 7, wherein said reflective member is provided with a mechanical hinge.

14. The ultrasonic imaging catheter apparatus of claim 7, wherein said electroactive polymer actuator comprises an electroactive polymer region, a counter-electrode region, and an electrolyte-containing region disposed between said electroactive polymer region and said counter-electrode region.

15. The ultrasonic imaging catheter apparatus of claim 7, wherein said electroactive polymer actuator comprises an electroactive polymer selected from polyaniline, polysulfone, polyacetylene and polypyrrole.

16. The ultrasonic imaging catheter apparatus of claim 8, farther comprising a motor and a drive shaft, said drive shaft translating torque from said motor to rotate said reflective member.

17. The ultrasonic imaging catheter apparatus of claim 7, comprising a plurality of electroactive polymer actuators, wherein said plurality of electroactive polymer actuators are adapted to change the angle of incidence of said ultrasonic energy relative to said reflective member.

* * * * *

UNITED STATES PATENT AND TRADEMARK OFFICE
CERTIFICATE OF CORRECTION

PATENT NO.        : 7,077,808 B2
APPLICATION NO.   : 10/631872
DATED             : July 16, 2006
INVENTOR(S)       : Lucien Alfred Couvillon, Jr.

It is certified that error appears in the above-identified patent and that said Letters Patent is hereby corrected as shown below:

Correction is requested for the following Applicant errors:

Specification, Col. 1, line 3, after "THE" change "INVENITON" to -- INVENTION --.

Specification, Col. 1, line 23, before "advances", delete "In Spite of" and insert -- Despite --.

Specification, Col. 3, line 66, after "until" change "is" to -- it --.

Specification, Col. 4, line 59, after "with" delete -- within --.

Specification, Col. 4, line 65, before "an" change "within" to -- with --.

Specification, Col. 8, line 12, before "layers" change "actively" to -- active --.

Specification, Col. 10, line 48, after "anti-restenosis" change "drug" to -- drugs --.

Correction is requested for the following Patent Office errors:

Specification, Col. 3, line 67, after "axis", change "alpha" symbol to italic letter -- $a$ -- .

Specification, Col. 4, line 2, after "axis", change "alpha" symbol to italic letter -- $a$ -- .

Specification, Col. 4, line 4, after "axis", change "alpha" symbol to italic letter -- $a$ -- .

Specification, Col. 4, line 5, after "axis", change "alpha" symbol to italic letter -- $a$ -- .

Specification, Col. 4, line 8, after "axis", change "alpha" symbol to italic letter -- $a$ -- .

Specification, Col. 4, line 11, after "axis", change "alpha" symbol to italic letter -- $a$ -- .

Specification, Col. 4, line 16, after "axis", change "alpha" symbol to italic letter -- $a$ -- .

Specification, Col. 4, line 45, after "lumen", change "1" to italic number -- $1$ -- .

Specification, Col. 4, line 46, after "disc", change "d" to italic letter -- $d$ -- .

UNITED STATES PATENT AND TRADEMARK OFFICE
CERTIFICATE OF CORRECTION

| | |
|---|---|
| PATENT NO. | : 7,077,808 B2 |
| APPLICATION NO. | : 10/631872 |
| DATED | : July 16, 2006 |
| INVENTOR(S) | : Lucien Alfred Couvillon, Jr. |

It is certified that error appears in the above-identified patent and that said Letters Patent is hereby corrected as shown below:

Correction is requested for the following Patent Office errors (cont'd):

Specification, Col. 5, line 29, after "axis", change "a" to italic letter -- *a* --.

Specification, Col. 7, line 10, after "occurs", change "in vivo" to -- *in vivo* --.

Claim 1, Col. 11, line 2, after "said", change "wail" insert -- wall --.

Claim 16, Col. 12, line 33, before "comprising", change "farther" to -- further --.

Add Claims 18-21 as follows:

18. A method of scanning the inner wall of a body lumen comprising:

providing the catheter apparatus of claim 9, sweeping said ultrasonic energy in a predetermined pattern over the interior wall of the body lumen, wherein said sweeping is accomplished by rotating said reflective member and operating said electroactive polymer actuator to change the angle of incidence of said ultrasonic energy relative to said reflective member; receiving ultrasonic energy reflected from the interior wall of the body lumen; and producing an image from the reflected ultrasonic energy.

19. The method of claim 19, wherein the ultrasonic energy is directed at a forward angle of from about 10° to about 85° relative to the axis of the body lumen, whereby a forward conical sweep is performed.

20. The method of claim 19, further comprising axially advancing the reflective member within the body lumen.

UNITED STATES PATENT AND TRADEMARK OFFICE
CERTIFICATE OF CORRECTION

| | | |
|---|---|---|
| PATENT NO. | : 7,077,808 B2 | |
| APPLICATION NO. | : 10/631872 | |
| DATED | : July 16, 2006 | |
| INVENTOR(S) | : Lucien Alfred Couvillon, Jr. | |

It is certified that error appears in the above-identified patent and that said Letters Patent is hereby corrected as shown below:

Add Claims 18-21 as follows (cont'd):

21. The method of claim 19, wherein the reflective member is rotated under electronic control.

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,077,808 B2 |
| APPLICATION NO. | : 10/631872 |
| DATED | : July 18, 2006 |
| INVENTOR(S) | : Lucien Alfred Couvillon, Jr. |

It is certified that error appears in the above-identified patent and that said Letters Patent is hereby corrected as shown below:

Correction is requested for the following Applicant errors:

Specification, Col. 1, line 3, after "THE" change "INVENITON" to -- INVENTION --.

Specification, Col. 1, line 23, before "advances", delete "In Spite of" and insert -- Despite --.

Specification, Col. 3, line 66, after "until" change "is" to -- it --.

Specification, Col. 4, line 59, after "with" delete -- within --.

Specification, Col. 4, line 65, before "an" change "within" to -- with --.

Specification, Col. 8, line 12, before "layers" change "actively" to -- active --.

Specification, Col. 10, line 48, after "anti-restenosis" change "drug" to -- drugs --.

Correction is requested for the following Patent Office errors:

Specification, Col. 3, line 67, after "axis", change "alpha" symbol to italic letter -- $a$ -- .

Specification, Col. 4, line 2, after "axis", change "alpha" symbol to italic letter -- $a$ -- .

Specification, Col. 4, line 4, after "axis", change "alpha" symbol to italic letter -- $a$ -- .

Specification, Col. 4, line 5, after "axis", change "alpha" symbol to italic letter -- $a$ -- .

Specification, Col. 4, line 8, after "axis", change "alpha" symbol to italic letter -- $a$ -- .

Specification, Col. 4, line 11, after "axis", change "alpha" symbol to italic letter -- $a$ -- .

Specification, Col. 4, line 16, after "axis", change "alpha" symbol to italic letter -- $a$ -- .

Specification, Col. 4, line 45, after "lumen", change "1" to italic number -- $1$ -- .

Specification, Col. 4, line 46, after "disc", change "d" to italic letter -- $d$ -- .

UNITED STATES PATENT AND TRADEMARK OFFICE
CERTIFICATE OF CORRECTION

| | | |
|---|---|---|
| PATENT NO. | : 7,077,808 B2 | |
| APPLICATION NO. | : 10/631872 | |
| DATED | : July 18, 2006 | |
| INVENTOR(S) | : Lucien Alfred Couvillon, Jr. | |

It is certified that error appears in the above-identified patent and that said Letters Patent is hereby corrected as shown below:

Correction is requested for the following Patent Office errors (cont'd):

Specification, Col. 5, line 29, after "axis", change "a" to italic letter -- *a* --.

Specification, Col. 7, line 10, after "occurs", change "in vivo" to -- *in vivo* --.

Claim 1, Col. 11, line 2, after "said", change "wail" insert -- wall --.

Claim 16, Col. 12, line 33, before "comprising", change "farther" to -- further --.

Add Claims 18-21 as follows:

18. A method of scanning the inner wall of a body lumen comprising:

providing the catheter apparatus of claim 9, sweeping said ultrasonic energy in a predetermined pattern over the interior wall of the body lumen, wherein said sweeping is accomplished by rotating said reflective member and operating said electroactive polymer actuator to change the angle of incidence of said ultrasonic energy relative to said reflective member; receiving ultrasonic energy reflected from the interior wall of the body lumen; and producing an image from the reflected ultrasonic energy.

19. The method of claim 19, wherein the ultrasonic energy is directed at a forward angle of from about 10° to about 85° relative to the axis of the body lumen, whereby a forward conical sweep is performed.

20. The method of claim 19, further comprising axially advancing the reflective member within the body lumen.

UNITED STATES PATENT AND TRADEMARK OFFICE
CERTIFICATE OF CORRECTION

PATENT NO.       : 7,077,808 B2
APPLICATION NO.  : 10/631872
DATED            : July 18, 2006
INVENTOR(S)      : Lucien Alfred Couvillon, Jr.

It is certified that error appears in the above-identified patent and that said Letters Patent is hereby corrected as shown below:

Add Claims 18-21 as follows (cont'd):

21. The method of claim 19, wherein the reflective member is rotated under electronic control.

This certificate supersedes Certificate of Correction issued October 2, 2007.

Signed and Sealed this

Thirtieth Day of October, 2007

JON W. DUDAS
*Director of the United States Patent and Trademark Office*